United States Patent [19]

Welte et al.

[11] 4,006,124

[45] Feb. 1, 1977

[54] AMIDINE-METAL COMPLEXES AND THEIR USE AS CATALYSTS FOR ISOCYANATE POLYADDITION REACTIONS

[75] Inventors: Rainer Welte, Bensberg-Herkenrath; Gerhard Grögler, Leverkusen, both of Germany

[73] Assignee: Bayer Aktiengesellschaft, Leverkusen, Germany

[22] Filed: June 26, 1975

[21] Appl. No.: 590,768

[30] Foreign Application Priority Data

July 16, 1974 Germany ............................ 2434185

[52] U.S. Cl. .................. 260/77.5 AC; 260/2.5 AC
[51] Int. Cl.[2] ....................................... C08G 18/00
[58] Field of Search ............. 260/77.5 AC, 2.5 AC

[56] References Cited

UNITED STATES PATENTS

| | | | |
|---|---|---|---|
| 3,252,945 | 5/1966 | Ugi et al. .................... | 260/77.5 AC |
| 3,769,244 | 10/1973 | Hashimoto et al. .... | 260/77.5 AC X |
| 3,814,707 | 6/1974 | Moller et al. .......... | 260/77.5 AC X |

*Primary Examiner*—Lewis T. Jacobs
*Attorney, Agent, or Firm*—Gene Harsh; Joseph Gil

[57] ABSTRACT

The instant invention is directed to a process for the production of novel amidine-metal complexes and to the use thereof as catalysts for isocyanate polyaddition reactions. The novel amidine-metal complexes of the instant invention are generally produced by mixing an amidine with a metal salt.

4 Claims, No Drawings

AMIDINE-METAL COMPLEXES AND THEIR USE AS CATALYSTS FOR ISOCYANATE POLYADDITION REACTIONS

BACKGROUND OF THE INVENTION

The art has been and is continually searching for new and more effective catalysts for use in isocyanate polyaddition reactions.

Numerous heavy metal compounds are effective catalysts for isocyanate polyaddition reactions and polyurethane formation. Amines are known to be similarly effective [see, e.g., K. C. Frisch and L. P. Rennao, "Catalysis in Isocyanate Reactions" in J. Macromol. Sci. — Revs. Macromol. Chem. C 5 (1), 103–150 (1970)].

The most active amines such as 1,4-diazabicyclo-(2,2,2)-octane have to be used in concentrations of from 0.04 to 0.5 parts by weight, based on the polyol, whereas other amines have to be used in considerably larger quantities when aliphatic isocyanates are used. However, even these small quantities of amine catalyst involve serious disadvantages. Thus, many of the amine catalysts are relatively volatile (e.g., 1,4-diazabicyclo-(2,2,2)-octane) and are still noticeable as a result of their pungent odor long after they have been prepared. This applies in particular to every day articles such as upholstery materials, trim for motor vehicles, shoes, furniture and the like. These amines are also frequently responsible for the yellowing of light-colored leather or plastics surfaces.

It is also known that the two groups of catalysts, when combined, act synergistically, a property which is also generally utilized on a commercial scale (see, e.g., J. H. Saunders and K. C. Frisch, Polyurethanes, Part I, Interscience Publishers, New York - London - Sydney, 1962, pp. 231 and 232).

The use of bicyclic amidines as polyurethane catalysts is described in German Offenlegungsschrift 1,745,418. The reference further indicates the desirability of the simultaneous use of organometallic compounds and the tricyclic amidines. German Offenlegungsschrift 1,950,262 describes amidines used as catalysts when aliphatic isocyanates are used in the addition reaction.

Amidines have the disadvantage that they are readily decomposed by water (cf. Houben-Weyl-Muller, Methoden der organischen Chemie, published by G. Thieme, Stuttgart, Vol. XI, page 940). This largely precludes their use in water-blown systems since even the small quantities of water always present in polyols are sufficient to considerably reduce the activity of free amidines within a few days. Accordingly, it has not been possible to store a polyol mixture containing an amidine catalyst. In a similar way, the presence of halogenated hydrocarbons, such as $CH_2Cl_2$, $CHCl_3$, $CCl_4$, $HClC=CClH$, $HClC=CCl_2$, or $H_2ClC-CClH_2$ seriously restricts the use of free amidines. They tend to react very quickly through quaternization which renders the amidines substantially ineffectual as catalysts.

DESCRIPTION OF THE INVENTION

It has now surprisingly been found that amidine-metal complexes obtainable simply by combining amidines of the type defined below with metal compounds of the type defined below represent outstanding catalysts for the isocyanate polyaddition reaction which are not attended by any of the disadvantages referred to above and which show in particular the following advantages:

1. Foams produced with the new complexes do not have any noticeable amine odor. The volatility of the complexes is so low that even extremely sensitive white-colored surfaces do not undergo and yellowing in contact with foams so-produced.

2. In contrast to the corresponding free amidines and also in contrast to many of the known metal compounds, the new complexes may be stored both in the presence of water and in the presence of chlorinated hydrocarbons. It is this property which distinguishes the new complexes and their use with particular advantage from the products and processes described in German Offenlegungsschrift 1,745,418, in which amidines and metal compounds are separately added to the reaction mixture in the production of polyurethanes.

3. Easier mold release is obtained when the new amidine-metal complexes are used for the production of moldfoamed plastics. This property distinguishes them with particular advantage from the combinations of 1,4-diazabicyclo-(2,2,2)-octane and organic tin (IV) compounds hitherto preferably used as catalysts.

4. Better reproducibility in the required mechanical properties of polyurethane foams is obtained by using the new amidine-metal complexes compared with the separate use of the individual components.

Accordingly, the present invention relates to a process for the production of amidine-metal complexes suitable for use as catalysts in the isocyanate polyaddition reaction, which is distinguished by the fact that amidines containing the characteristic group

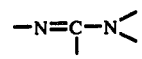

are mixed, optionally in the presence of an inert solvent, with 0.25 to 2 times the molar quantity of a metal compound corresponding to the formula

in which:
Me represents an $(n + m)$-valent metal,
X represents an aliphatic hydrocarbon radical having 1 to 18 carbon atoms, an aromatic hydrocarbon radical having 6 to 10 carbon atoms or an araliphatic hydrocarbon radical having 7 to 15 carbon atoms,
Y represents an aliphatic $C_2$–$C_{18}$-carboxylate anion having a single negative charge and optionally containing olefinic double bonds and/or alcoholic hydroxyl groups, or a $C_5$–$C_{18}$-enolate anion having a single negative charge,
$n = 0$ to 2,
$m = 0$ to 4 with the proviso that $n + m$ together $= 2$ to 4.

The invention also relates to the use of the amidine-metal complexes obtainable by this process as catalysts for the isocyanate polyaddition reaction.

The amidines used in the process according to the instant invention include any organic compound which contains at least one characteristic amidine group of the formula:

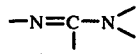

but which does not contain any bulky substituents which because of steric hindrance have an inhibiting effect either upon complex formation or upon the isocyanate polyaddition reaction or contain substituents with functional groups reacting with isocyanates such as —COOH or —SO$_3$H. The following are preferred examples of amidines of this kind:

1. Amidines corresponding to the formula:

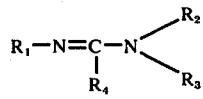

in which:

$R_1$, $R_2$ and $R_3$ are the same or different and represent hydrogen, an aliphatic hydrocarbon radical having 1 to 18 carbon atoms, preferably having 1 to 4 carbon atoms, an aromatic hydrocarbon radical having 6 to 10 carbon atoms, preferably a benzyl radical, an araliphatic hydrocarbon radical having 7 to 10 carbon atoms, preferably a phenyl radical or a cycloaliphatic hydrocarbon radical having 5 to 7 carbon atoms, preferably a cyclohexyl radical, with the proviso that at most only one of the radicals $R_1$ to $R_3$ represents hydrogen, $R_4$ represents a radical $R_1$ or a radical —N($R_2$) ($R_3$).

Examples of amidines such as these include N,N'-dimethyl-formamidine, N,N'-dimethylacetamidine, trimethyl acetamidine, N,N'-dimethylformamidine, N-benzyl-N,N'-dimethylacetamidine, N,N'-dimethyl-N-ethylbenzamidine, N,N'-dicyclohexyl-N-methylacetamidine, triphenyl benzamidine, N,N'-diphenyl-N'-methyl benzylamidine, tetramethyl guanidine. N,N'-diphenyl-N,N'-dimeethyl guanidine or tetraphenyl guanidine.

The production of amidines of this kind is known and is described comprehensively with general procedures and specific examples in Houben-Muller-Weyl, Methoden der Organischen Chemie, Vol. XI, 2, pp. 38–66, Verlag G. Thieme, Stuttgart 1958.

The production of guanidine derivatives of the aforementioned kind is also known and is described comprehensively with general procedures and specific examples in Houben-Muller-Weyl, Methoden der Organischen Chemie, Vol. VIII, pp. 180–188, Verlag G. Thieme, Stuttgart 1958.

2. Monocyclic amidines corresponding to the formula:

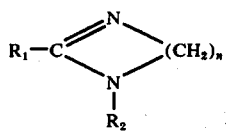

in which:

$R_1$ and $R_2$ are as defined with reference to formula (I), and $n$ is an integer from 2 to 4.

Examples of monocyclic amidines of this kind include 2,3-dimethyl-3,4,5,6-tetrahydropyrimidine, N-methyl-Δ2-tetrahydropyrimidine, N-cyclohexyl-2-methyl-Δ2-tetrahydropyrimidine, N-benzyl-2-butyl-Δ2-tetrahydropyrimidine, 2-methyl-Δ2-imidazoline, 1,2-diphenyl-Δ2-imidazoline, 1-methyl-Δ4-1,2,4-triazoline and 1,5-dibutyl-Δ4-1,2,4-triazoline.

The production of cyclic amidines of this kind is also known and is described in Houben-Muller-Weyl, Methoden der Organischen Chemie, Vol. XI, 2, pages 38–66.

3. Imidazoles corresponding to the formula:

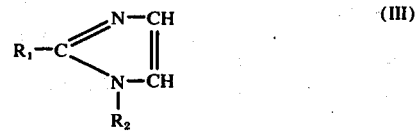

in which:

$R_1$ and $R_2$ are as defined with reference to formula (I).

Examples of imidazoles of this kind are N-methylimidazole, N-butylimidazole and 2,3-dimethylimidazole.

The production of imidazole derivatives of this kind is known and described, for example, by V. Anwers and Mauss, Ber. dtsch. Chem. Ges. 61, 2415 – 2418 (1928).

4. Monocyclic amidines (α-aminopyridines) corresponding to the formula:

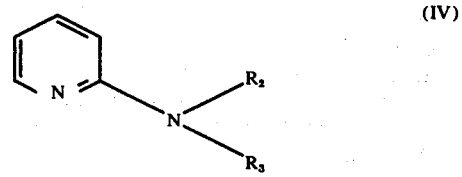

in which:

$R_2$ and $R_3$ are the same or different and represent hydrogen or an alkyl radical with 1 to 4 carbon atoms.

Examples of amidines of this kind are α-amino-pyridine, α-dimethylaminopyridine and α-dibutylaminopyridine, the production of which is described, for example, in German Pat. No. 489,184.

5. Bicyclic amidines corresponding to the formula:

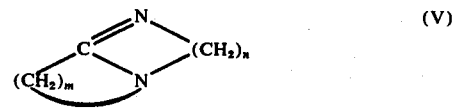

in which:

$n$ and $m$ are the same or different and represent integers from 2 to 4.

Examples of bicyclic amidines of this kind are 1,5-diazabicyclo-[4.3.0]-5-nonene, 1,5-diazabicyclo-[4.4.0]-5-decene or 1,8-diazabicyclo-[5.3.0]-7-decene. The production of bicyclic compounds of this kind is known and described, for example, in German Offenlegungsschrift 1,545,855.

In addition to the aforementioned amidines, metal compounds corresponding to the following formula are also used in the process according to the invention:

$$MeX_nY_m$$

In this formula,
Me represents an ($n + m$)-valent metal, preferably a metal from the Ist, IInd, VIIth Secondary Group, VIIIth or IVth Main Group of the Periodic System of Chemical Elements,
X represents an aliphatic hydrocarbon radical having 1 to 18 carbon atoms, an aromatic hydrocarbon radical having 6 to 10 carbon atoms or an araliphatic hydrocarbon radical having 7 to 15 carbon atoms,
Y represents an aliphatic $C_2$-$C_{18}$-carboxylate anion having a single negative charge and optionally containing olefinic double bonds and/or alcoholic hydroxyl groups, or a $C_5$-$C_{18}$-enolate anion having a single negative charge.
$n = 0$ to 2,
$m = 0$ to 4, with the proviso that $n + m$ together $= 2$ to 4.

Preferred metal compounds for the process according to the invention are metal compounds of trivalent iron, divalent nickel, divalent zinc, trivalent manganese, divalent tin or tetravalent tin. The following are examples of metal compounds suitable for use in the process according to the invention:

Fe(III)-acetate, Fe(III)-oleate, Fe(III)-stearate, Fe(III)-acetylacetonate, Zn-acetate, Zn-oleate, Zn-acetylacetonate, Mn(II)-acetate, Mn(II)-acetylacetonate, Mn(II)-palmitate, Mn(II)-versatate, Mn(II)-naphthenate, Sn(II)-acetate, Sn(II)-octoate, Sn(II)-isoctoate, Sn(II)-ricinoleate, Sn(II)-naphthenate, dibutyl-Sn(IV)-laurate, dibutyl-Sn(IV)-octoate, diethyl-Sn(IV)-2-methyl hexoate, diphenyl-Sn(IV)-caproate, Ni(II)-acetate, Ni(II)-octoate, Ni(II)-oleate, Ni(II)-ricinoleate, Ni(II)-acetylacetonate, Ni(II)-salicylate and Cu(II)-acetylacetonate.

The amidines and the metal compounds are used in the process according to the invention in a molar ratio of amidine to metal compound of from 0.5:1 to 4:1, and preferably from 1:1 to 3:1. The process according to the invention is carried out without difficulty simply by combining the components at temperatures in the range from 0° C to 120° C, preferably in the range from 0° C, providing one of the two components is liquid at temperatures in this range. The aforementioned temperature range is maintained by effective cooling, the components being combined in the absence of water or in an inert gas atmosphere, depending upon their sensitivity. In cases where both components are solids, one of the two components is preferably dissolved in an inert solvent, for example, benzene, toluene or xylene, and the other component added while cooling. The solvent is then removed, preferably in vacuo. Water or halogenated hydrocarbons, especially chlorinated hydrocarbons, should only be present after the exothermic reaction has completely abated.

Particularly preferred end products of the process are the complexes of 2,3-dimethyl-3,4,5,6-tetrahydropyrimidine and dibutyl tin dilaurate; 2,3-dimethyl-3,4,5,6-tetrahydropyrimidine and dibutyl tin-bis-ethyl hexoate, 2,3-dimethyl-3,4,5,6-tetrahydropyrimidine and diethyl tin diacetate; 2-methyl-3-cyclohexyl-3,4,5,6-tetrahydropyrimidine and dibutyl tin-dilaurate; 2,3-dimethyl-3,4,5,6-tetrahydropyrimidine and Mn(II)-acetylacetonate; 2,3-dimethyl-3,4,5,6-tetrahydropyrimidine and Ni(II)-acetylacetonate; N-methylimidazole and dibutyl tin dilaurate; N-methylimidazole and Mn(II)-acetylacetonate and N-methyl-imidazole and Fe(III)-acetylacetonate.

The amidine-metal complexes obtained by the process according to the invention are generally homogeneously soluble in low molecular weight or high molecular weight polyhydroxyl compounds, of the type used in the production of polyurethane plastics, although the new complexes can also be used in finely dispersed form. In the application of the new complexes in accordance with the invention, the new products are normally added to the polyol components used for the production of polyurethane plastics in quantities of from 0.001 to 4.00% by weight and preferably in quantities of from 0.01 to 0.8% by weight. The new catalysts can be used with advantage in the production of solid elastomers or for the production of polyurethane foams. The foams can be made in the form of hard, semi-hard or soft products in terms of their elasticity with unit weights varying from about 15 kg/m³ to about 1000 kg/m³.

The polyisocyanates suitable for the production of polyurethane plastics using the new complexes in accordance with the invention include any aliphatic, cycloaliphatic, araliphatic, aromatic and heterocyclic organic polyisocyanates of the type described, for example, by W. Siefken in Justus Liebigs Annalen der Chemie, 562, pp. 75 to 136. Specific examples include ethylene diisocyanate, 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate and mixtures of these isomers; 1-isocyanato-3,3,5-trimethyl-5-isocyanatomethyl cylcohexane, 2,4- and 2,6-hexahydrotolylene diisocyanate and mixtures of these isomers; hexahydro-1,3-and/or -1,4-phenylene diisocyanate; perhydro-2,4'-and/or -4,4'-diphenylmethane diisocyanate; 1,3- and 1,4-phenylene diisocyanate; 2,4- and 2,6-tolylene diisocyanate and mixture of these isomers; diphenyl-methane-2,4'- and/or -4,4'-diisocyanate; naphthylene-1,5-diisocyanate; triphenylmethane-4,4',-4''-triisocyanate; polyphenyl polymethylene polyisocyanates of the type obtained by condensing aniline with formaldehyde, followed by phosgenation, and described in British Pat. Nos. 874,430 and 848,671; perchlorinated aryl polyisocyanates of the type described in German Auslegeschrift 1,157,601; polyisocyanates containing carbodiimide groups of the type described in German Pat. No. 1,092,007; diisocyanates of the type described in U.S. Pat. No. 3,492,330; polyisocyanates containing allophonate groups of the type described in British Pat. No. 994,890, in Belgian Pat. No. 761,626, and in Published Dutch Patent Application No. 7,102,524; polyisocyanates containing isocyanurate groups of the type described in German Pat. Nos. 1,022,789; 1,222,067 and 1,027,394 and in German Offenlegungsschrifts Nos. 1,929,034 and 2,004,048; polyisocyanates containing urethane groups of the type described in Belgian Pat. No. 752,261 or in U.S. Pat. No. 3,394,164; polyisocyanates containing acylated urea groups as described in German Pat. No. 1,230,778; polyisocyanates containing biuret groups of the type described in German Pat. No. 1,101,394, in British Pat. No. 889,050 and in French Pat. No. 7,017,514; polyisocyanates obtained by telomerization reactions of the type described in Belgian Pat. 723,640; polyisocyanates containing ester groups of the type described in British Pat. Nos. 956,474 and 1,072,956, in U.S. Pat. No. 3,567,763 and in German Pat. No.

1,231,688; and, reaction products of the aforementioned isocyanates with acetals as described in German Pat. No. 1,072,385.

It is also possible to use the isocyanate-group-containing distillation residues accumulating in the production of ioscyanates on an industrial scale, optionally in solution in one or more of the aforementioned polyisocyanates. It is also possible to use any mixtures of the aforementioned polyisocyanates.

As a rule, it is particularly preferred to use readily available polyisocyanates such as 2,4- and 2,6-tolylene diisocyanate and mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates").

Other starting components suitable for use in the production of polyurethane plastics using the new complexes in accordance with the invention include compounds containing at least two isocyanate-reactive hydrogen atoms and generally having molecular weights of from 400 to 10,000. Such compounds include compounds containing amino groups, thiol groups, hydroxyl groups, or carboxyl groups. The presently preferred compounds of this kind are polyhydroxyl compounds, and more especially, polyhydroxyl compounds containing 2 to 8 hydroxyl groups having molecular weights in the range from 800 to 10,000, and preferably in the range from 1000 to 6000. Such polyhydroxyl compounds include polyesters, polyethers, polythioethers, polyacetals, polycarbonates, and polyester amides containing at least 2, generally 2 to 8 and preferably 2 to 4 hydroxyl groups of the type generally known for the production of homogeneous and cellular polyurethanes.

Suitable hydroxyl-group-containing polyesters include reaction products of polyhydric, preferably dihydric and, optionally, trihydric alcohols with polyvalent, and preferably divalent carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids can be aliphatic, cycloaliphatic, aromatic and/or heterocyclic and may be substituted (for example, by halogen atoms) and/or unsaturated. Examples of useful polycarboxylic acids include succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, such as oleic acid, optionally in admixture with monomeric fatty acids, terephthalic acid dimethyl ester and terephthalic acid bis-glycol ester. Examples of suitable polyhydric alcohols include ethylene glycol, 1,2-and 1,3-propylene glycol, 1,4- and 2,3-butylene glycol, 1,6-hexane diol, 1,8-octane diol, neopentyl glycol, cyclohexane dimethanol (1,4-bis-hydroxymethyl cyclohexane), 2-methyl-1,3-propane diol, glycerol, trimethylolpropane, 1,2,6-hexane triol, 1,2,4-butane triol, trimethylolethane, pentaerythritol, quinitol, mannitol and sorbitol, methyl glycoside, also diethylene glycol, triethylene glycol, tetraethylene glycol, polyethylene glycols, dipropylene glycol, polypropylene glycols, dibutylene glycol and polybutylene glycols. The polyesters may contain some terminal carboxyl groups. It is also possible to use polyesters of lactones such as ε-caprolactone, or of hydroxy carboxylic acids such as ω-hydroxy caproic acid.

Suitable polyethers containing at least 2, generally 2 to 8 and preferably 2 to 3 hydroxyl groups, are also generally known and can be obtained, for example, by polymerizing epoxides such as ethylene oxide, propylene oxide, butylene oxide, tetrahydrofuran, styrene oxide or epichlorhydrin alone in the presence of $BF_3$, or by adding these epoxides, optionally in admixture or in succession, to starter components containing reactive hydrogen atoms such as water, alcohols or amines. Examples of such starter components include ethylene glycol, 1,3- or 1,2-propylene glycol, trimethylol propane, 4,4'-dihydroxydiphenyl propane, aniline, ammonia, ethanolamine and ethylene diamine. Sucrose polyethers, of the type described in German Auslegeschrifts 1,176,358 and 1,064,938, can also be used in accordance with the invention. In many cases, it is preferred to use polyethers of the kind which contain substantial quantities of primary OH-groups (up to 90% by weight, based on all the OH-groups present in the polyether). Polyethers modified by vinyl polymers such as those produced by polymerizing styrene and/or acrylonitrile in the presence of polyethers (see, e.g. U.S. Pat. Nos. 3,383,351; 3,304,273; 3,523,093 and 3,110,695; German Pat. No. 1,152,536) are also suitable, as are polybutadienes containing OH-groups.

Among the polythio ethers, reference is made in particular to the condensation products of thiodiglycol alone and/or with other glycols, dicarboxylic acids, formaldehyde, aminocarboxylic acids or amino alcohols. The products are polythio mixed ethers, polythio ether esters or polythio ether ester amides, depending upon the cocomponents.

Examples of suitable polyacetals include the compounds obtainable from glycols, such as diethylene glycol, triethylene glycol, 4,4'-dioxethoxy diphenyl dimethyl methane, hexane diol and formaldehyde. Polyacetals suitable for use in accordance with the invention can also be obtained by polymerizing cyclic acetals.

Suitable polycarbonates containing hydroxy groups are known and include those which can be obtained, for example, by reacting diols such as 1,3-propane diol, 1,4-butane diol and/or 1,6-hexane diol, diethylene glycol, triethylene glycol or tetraethylene glycol, with diaryl carbonates such as diphenyl carbonate, or phosgene.

The polyester amides and polyamides include the predominantly linear condensates obtained from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and optionally modified natural polyols such as castor oil, carbohydrates and starch, can also be used. Addition products of alkylene oxides with phenol-formaldehyde resins or even with urea-formaldehyde resins, can also be used in accordance with the invention.

Examples of the many and varied compounds which can be used as described, for example, in High Polymers, Vol. XVI, "Polyurethanes, Chemistry and Technology", Saunders-Frisch, Interscience Publishers, New York, London, Vol. I, 1962, pp. 32–42 and pp. 44–54, and Vol. II, 1964, pp. 5–6 and 198–199, and in Kunststoff-Handbuch, Vol. VII, Vieweg-Hochtlen, Carl-Hanser-Verlag, Munich, 1966, pages 45 to 71.

In many cases, the production of polyurethane plastics using the new complexes in accordance with the invention is carried out in the presence of water and/or readily volatile organic substances as blowing agents. Examples of suitable organic blowing agents include acetone; ethylacetate; methanol; ethanol; halogen-substituted alkanes such as methylene chloride, chloroform, ethylidene chloride, vinylidene chloride, monofluorotrichloromethane, chlorodifluoromethane, and dichlorodifluoromethane; butane; hexane; heptane; or diethyl ether. A blowing effect can also be obtained by adding compounds which decompose giving off gases, (e.g., nitrogen) at temperatures above room temperature, which compounds include azo compounds such as azoisobutyronitrile. Further examples of blowing agents and particulars on the use of blowing agents may be found in Kunststoff-Handbuch, Vol. VII, published by Vieweg and Hochtlen, Carl-Hanser-Verlag, Munich, 1966, pages 108 to 109, 453 to 455 and 507 to 510.

In addition to the described complexes, it is also possible in accordance with the invention to add other catalysts whereby special effects can be obtained. Examples of suitable co-catalysts include the catalysts known per se, such as tertiary amines such as triethylamine, tributylamine, N-methyl morpholine, N-ethyl morpholine, N-coco morpholine, N,N,N',N'-tetramethyl ethylene diamine, 1,4-diazabicyclo-(2,2,2)-octane,N-methyl-N'-dimethylaminoethyl piperazine, N,N-dimethylbenzylamine, bis-(N,N-diethylaminoethyl)-adipate, N,N-diethylbenzylamine, pentamethyl diethylene triamine, N,N-dimethyl cyclohexylamine, N,N,N',N'-tetramethyl-1,3-butane diamine, N,N-dimethyl-β-phenylethylamine, 1,2-dimethyl-imidazole and 2-methylimidazole.

Tertiary amines containing isocyanate-reactive hydrogen atoms are also suitable and include triethanolamine, triisopropanolamine, N-methyl diethanolamine, N-ethyl diethanolamine, N,N-dimethyl ethanolamine and their reaction products with alkylene oxides such as propylene oxide and/or ethylene oxide.

Other suitable co-catalysts include silaamines with carbon-silicon bonds of the type described in German Pat. No. 1,229,290. Examples include 2,2,4-trimethyl-2-silamorpholine and 1,3-diethylaminomethyl tetramethyl disiloxane.

It is also possible to use tetraalkyl ammonium hydroxides, alkali hydroxides, phenolates, or alcohols with the described complexes.

It is, of course, also possible to use mixtures of different complexes according to the invention or to add other organometallic components whereby additional reactions known per se can be catalyzed in this way. For example, dimerization, trimerization, carbodiimide, allophanatization and biuret formation of the isocyanates can be catalyzed in this way.

The additional catalysts are added in quantities of from 0 to 90% of the total quantity of catalyst, and preferably in quantities of from 0 to 50%.

The production of polyurethane plastics using the new complexes in accordance with the invention can also be carried out in the presence of surface-active additives (emulsifiers and/or foam stabilizers). Examples of emulsifiers include the sodium salts of castor oil sulphonates or fatty acids; and salts of fatty acids with amines, such as oleic acid/diethylamine or stearic acid/diethanolamine. Alkali or ammonium salts of sulphonic acids such as dodecyl benzene sulphonic acid or dinaphthyl methane disulphonic acid; of fatty acids such as ricinoleic acid; or of polymeric fatty acids, can also be used as surface-active additives.

Suitable foam stabilizers include water-soluble polyether siloxanes generally known in the art. These compounds are generally synthesized in such a way that a copolymer of ethylene oxide and propylene oxide is attached to a polydimethyl siloxane radical. Foam stabilizers of this kind are described, for example, in U.S. Pat. No. 3,201,372.

Reaction retarders, such as acid-reacting substances such as hydrochloric acid or organic acid halides; cell regulators such as paraffins, fatty alcohols, or dimethyl polysiloxanes; pigments; dyes; flameproofing agents such as tris-chloroethyl phosphate or ammonium phosphate and polyphosphate; stabilizers against ageing and weathering; plasticizers; fungistatic and bacteriostatic agents; and fillers such as barium sulphate, kieselguhr, carbon black or whiting can also be used.

Further examples of the many different types of surface-active additives and foam stabilizers, cell regulators, reaction retarders, stabilizers, flameproofing agents, plasticizers, dyes and fillers, fungistatic and bacteriostatic agents, optionally used in accordance with the invention, and details on the way in which additives of this kind are used and the manner in which they work, can be found in Kunststoff-Handbuch, Vol. VI, published by Vieweg and Hochtlen, Carl-Hanser-Verlag, Munich, 1966, pages 103 to 113.

The reaction components are reacted by the one-stage process known per se, by the prepolymer process or by the semi-prepolymer process, often using machines, such as those of the type described in U.S. Pat. No. 3,201,372. Details of processing machines which may also be used in accordance with the invention may be found in Kunststoff-Handbuch, Vol. VI, published by Vieweg and Hochtlen, Carl-Hanser-Verlag, Munich, 1966, pages 121–205.

By using the new complexes in accordance with the invention as catalysts in the production of polyurethanes, it is possible to considerably reduce the total quantity of amine necessary without impairing the catalytic effect. The reduction in the quantity of amine is of particular advantage in cases where the hitherto used quantities of free amine have been noticeable by their pungent odor long after the production of the polyurethane. This applies in particular to every day articles such as upholstery materials, trim for motor vehicles, shoes, furniture, and the like. In many cases, yellowing is also attributable to the volatility of free amines, whereas the complexes according to the invention have no measurable vapor pressure at room temperature (see Examples 6 and 11, herein).

The advantages of the complexes according to the invention over the free amidines previously described include the fact that they are inert both with respect to water and also with respect to halogenated hydrocarbons (see Example 6, herein). Even after storage for 6 months, reactive mixtures produced according to Example 1 do not show any decrease in reactivity, although the quantity of water always present in the polyether, amounting to approximately 0.05%, is more than enough to hydrolyze the amidine. Accordingly, the complexes according to the invention can be directly added during formulation of the polyol mixture. This eliminates the need for a subsequent operation or for an additional metering unit in the mixing head.

The complexes according to the invention generally have to be prepared before addition to the polyol. Addition of the components individually produces much poorer results (see Example 8).

One particular advantage of the catalysts according to the instant invention is that, although their effect is developed with some delay, they very quickly become highly active, especially in the final hardening phase. So far as practical application is concerned, this affords the advantage of a relatively long period during which the foamable mixture is liquid, but of a short hardening time after the onset of the exothermic reaction. This particular advantage is most important in industrial processes where short in-mold times are required. In Examples 1 to 4, this is illustrated by the difference $T_4 - T_1$. The smaller this difference, the more quickly a molding can be mold-released.

EXAMPLE 1

A semi-hard freely foamed polyether foam was produced, having a unit weight of approximately 400 g/dm$^3$. $T_1$ = beginning of the blowing reaction, $T_2$ = end of the blowing reaction, $T_3$ = tack-free time, $T_4$ = hardening time (after which it is no longer possible to tear out parts of the foam by hand).

Recipe:
70 g of bifunctional polypropylene oxide, OH-number 27.5 (obtained by propoxylating propylene glycol, approximately 10% by weight of ethylene oxide being grafted on at the end).
20 g of trifunctional polypropylene oxide, OH-number 35.4 (obtained by propoxylating trimethylol propane, 10% by weight of ethylene oxide being grafted on at the end).
8 g of 1,4-butane diol
12 g of trichlorofluoromethane
0.054 g of complex 1 (this corresponds to 0.04 g of dibutyl tin dilaurate + 0.014 g of 2,3-dimethyl-3,4,5,6-tetrahydropyrimidine; the components were combined at 20° C by adding the amidine dropwise with stirring to the dibutyl tin dilaurate).

The components are carefully mixed for 30 seconds at 25° C using a high-speed stirrer, after which 76.7 g of diphenylmethane diisocyanate are added and the mixture stirred for 15 seconds. The following values are obtained in an open cardboard cup:

$T_1 = 30 \pm 3$ seconds
$T_2 = T_3 = 45 \pm 3$ seconds
$T_4 = 50 \pm 5$ seconds

EXAMPLE 2 (Comparison)

For comparision, the same foam is catalyzed with 0.014 g of triethylene diamine and 0.04 g of dibutyl tin dilaurate. The following results are obtained:

$T_1 = 55 \pm 5$ seconds
$T_2 = T_3 = 100 \pm 10$ seconds
$T_4 = 140 \pm 10$ seconds

EXAMPLE 3 (Comparison)

In order to obtain results similar to those of Example 1 with the catalysts mentioned in Example 2, it is necessary to use the following quantities of catalyst: 0.04 g of dibutyl tin dilaurate + 0.065 g of triethylene diamine.

The following times are obtained in this way:

$T_1 = 20 \pm 2$ seconds
$T_2 = T_3 = 140 \pm 5$ seconds
$T_4 = 50 \pm 5$ seconds

EXAMPLE 4 (Comparison)

In order to obtain the same starting time as in Example 1, the following quantities of catalysts had to be used: 0.04 g of dibutyl tin dilaurate + 0.02 g of triethylene triamine.

The following times are obtained in this way:

$T_1 = 30 \pm 3$ seconds
$T_2 = T_3 = 50$ seconds
$T_4 = 65 \pm 5$ seconds

EXAMPLE 5

82 g of N-methylimidazole are added dropwise with cooling at 25° C to 632 g of dibutyl tin dilaurate, the required complex being formed in an exothermic reaction. After 2 hours, the reaction is complete. The reaction is quantitative, as shown by comparison of the NMR-spectra of the product formed with that of the free methylimidazole: NMR-spectrum of the free N-methylimidazole:

$\delta = 3.05$ ppm, 3 protons; $\delta = 6.65$ ppm, 1 proton; $\delta = 7.10$ ppm, 1 proton; $\delta = 7.25$ ppm, 1 proton.

After completion of the reaction, this spectrum has completely disappeared, and the following signals are now found:

$\delta = 2.82$ ppm, 3 protons; $\delta = 6.40$ ppm, 1 proton; $\delta = 7.20$ ppm*, $\delta = 7.35$ ppm*; $\delta = 7.65$ ppm*;
* These three signals correspond together to 2 protons.

The multiple of the butyl and lauryl groups is found between $\delta = 0.7$ ppm and $\delta = 2.6$ ppm.

EXAMPLE 6

112 g of 2,3-dimethyl-3,4,5,6-tetrahydropyrimidine are added dropwise with cooling to 632 g of dibutyl tin dilaurate. The required complex is formed in an exothermic reaction. Whereas 2,3-dimethyl-3,4,5,6-tetrahydropyrimidine in its free form boils at 70° C/0.1 mm, no volatile product is obtained from the complex formed at temperatures of up to 200° C/0.1 mm, nor are there any decomposition products beyond that temperature. This demonstrates the high thermal stability of the complex.

The IR-spctrum shows the spectrum of a new compound: whereas the amine shows only a single IR-band between 1500 cm$^{-1}$ and 2000 cm$^{-1}$ at 1620 cm$^{-1}$ and the dibutyl tin dilaurate shows a single band at 1600 cm$^{-1}$, the complex shows three bands of equal intensity at 1560 cm$^{-1}$, 1610 cm$^{-1}$ and 1650 cm$^{-1}$. Two very sharp bands of the amine at 940 cm$^{-1}$ and 1010 cm$^{-1}$ are no longer present, nor is there any superposition, only a new spectrum, in the fingerprint region. The NMR-spectrum of the product also shows significant differences compared to that of the starting compounds.

A foam is prepared using this complex in accordance with Example 1. In a second test, another part of the complex is dissolved in methylene chloride and the resulting solution stored for a few hours at room temperature. After the methylene chloride has been distilled off in vacuo, the complex is recovered. The IR-spectrum is the same. The use of this distillation residue in the production of a foam in accordance with Example 1 gives identical values of $T_1$, $T_2$, $T_3$ and $T_4$.

If by contrast, free 2,3-dimethyl-3,4,5,6-tetrahydropyrimidine is dissolved in $CH_2Cl_2$ or $CCl_4$, an exothermic reaction is observed. After the solvent has been distilled off, the IR-spectrum is totally different.

If The residual substance is reused together with the corresponding quantity of dibutyl tin dilaurate in a foam mixture according to Example 1, the following values are obtained:

$T_1$ = 50 seconds
$T_2$ = 85 seconds
$T_3$ = 95 seconds
$T_4$ = > 300 seconds

The value of $T_4$ indicates inadequate hardening of the foam. The same values are obtained when only dibutyl tin dilaurate is used as catalyst in Example 1.

EXAMPLE 7

In order to compare the influence of the amidine ligand upon reactivity, complexes all having the same central atom, namely, Sn(IV), were prepared. The foams were prepared from the same recipe as in Example 1. The quantity of catalyst, starting time and setting time were compared.

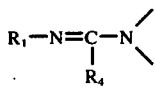

*Quantity of complex, based on 100 g of polyol mixture (before addition of the isocyanate)

In order to determine the influence of the central atom, a few metal compounds were reacted with the same amidine, namely, 2,3-dimethyl-3,4,5,6-tetrahydropyrimidine, and the complexes tested in producing a foam similar to Example 1. Starting time and setting time:

Example 1.

| Metal compound | Catalyst/ 100 g of polyol (g) | Starting time (seconds) | Setting time (seconds) |
|---|---|---|---|
| Tin(II)octoate | 0.6 | 28 | 120 |
| Hg(II)acetate | 0.3 | 35 | 130 |
| Zn-acetate | 0.6 | 30 | 75 |
| Zn-acetylacetonate | 0.6 | 25 | 63 |
| Zn-oleate | 0.6 | 35 | 100 |
| Mg(II)acetylacetonate | 0.2 | 10 | 45 |
| Cu(II)acetylacetonate | 0.6 | 50 | 140 |

Example 1.-continued

| Metal compound | Starting time and setting time: Catalyst/ 100 g of polyol (g) | Starting time (seconds) | Setting time (seconds) |
|---|---|---|---|
| Fe(II)acetylacetonate | 0.4 | 68 | 75 |

EXAMPLE 8

50 g of a trifunctional polypropylene oxide ether (obtained by propoxylating dipropylene glycol with 10% by weight of ethylene glycol grafted on at the end, OH-number 35), 1.5 g of $H_2O$, 0.5 g of a polyether-polysiloxane foam stabilizer (obtained by cohydrolysis of a mixture of bromomethylmethyldichlorosilane, dimethyl-dichlorsilane and bromethyldimethyl-chlorosilane, followed by reacting the product with cyclohexyl amine and reacting the aminomethylpolysiloxane thus formed with a bischloroformiate from phosgene and a copolyether of ethylene oxide and propylene oxide) and 0,05 g of complex according to Example 6, are carefully mixed with a high-speed stirrer. 18.0 g of tolylene diisocyanate (80% of 2,4- and 20% of 2,6-isomer) are then added, and the mixture is stirred for 15 seconds and then poured into a cardboard cup. Foaming begins after 20 seconds, being complete after about 120 seconds. Brief hardening at 100° C completes the setting reaction. A fine-pored open-cell soft foam with a unit weight of approximately 35 kg/m³ is obtained.

If, instead of the complex, the corresponding quantities of the individual components are successively added (first about 0.008 g of 2,3-dimethyl tetrahydropyrimidine and then approximately 0.042 g of dibutyl tin dilaurate), a foam is obtained which collapses immediately after the beginning of the foaming reaction and does not give a product of any commercial value.

EXAMPLE 9

50 g of a polyester of diethylene glycol, trimethylolpropane and adipic acid (OH-number of 60), 1 g of castor oil sulphonate, 0.5 g of the polyether-polysiloxane foam stabilizer of Example 8, 1.25 g of $H_2O$ and 0.1 g of the complex of Example 5 are homogenized. 22.5 g of toluene diisocyanate (65 mol % of 2,4-isomer and 35 mol % of 2,6-isomer) are then added, followed by mixing for 10 seconds with a high-speed stirrer. Foaming begins after 14 seconds and is over after 70 seconds. The foam reaches its final hardness in 3 minutes at approximately 80° C.

In a comparison test, dimethyl butylamine was used as catalyst. In order to obtain results comparable to the process according to invention it was necessary to use 0,6 g of catalyst (6-times the amount of the complex) which gave rise to a very unpleasant smell of the reaction mixture. Moreover, $T_1$ was somewhat smaller and $T_4$ greater than when using the complex according to the invention: Foaming began after 10 seconds and was over after 82 seconds. In this case, too, the foam hardened over a period of 3 minutes at 80° C.

EXAMPLE 10

20 parts of a polyester of adipic acid, phthalic acid anhydride, oleic acid and trimethylolpropane (OH-number 370), 30 parts of trifunctional polypropylene oxide ether (OH-number 460), 1.5 parts of castor oil sulphonate, 0.5 parts of the polyether-polysiloxane foam stabilizer of Example 8, 10 g of monofluorotrichloromethane and 0.2 g of catalyst according to Example 5, are homogenized. 32 g of crude diphenyl methane diisocyanate (NCO-content 31%, viscosity/20° C: 200 cP) are then added and the mixture stirred for 15 minutes with a high-speed stirrer. The following values are obtained in an open vessel.

$T_1$ = 34 seconds,
$T_2$ = 95 seconds.
$T_3$ = 95 seconds.

The symbols $T_1$, $T_2$ and $T_3$ have the same meaning as in Example 1. The hard foam formed has a fine, uniform closed cell structure.

EXAMPLE 11

50 g of a mixture according to Example 1 are introduced into a glass flask and a piece of white-colored leather inserted loosely into its neck. A second flask is filled with 50 g of a mixture according to Example 2, and an identical piece of leather inserted into its neck, while a third flask is filled with a similar mixture, but with 2,3-dimethyl-3,4,5,6-tetrahydropyrimidine as the only catalyst, and a piece of white leather similarly introduced into its neck.

When the flasks are placed in a drying cabinet for 30 minutes at 70° C, the leather according to Example 1 is unchanged, while the two other pieces of leather turn brown in color. After another 4 hours at 70° C, the leather according to Example 1 is still white in color, while the brown color of the other two pieces of leather has become even darker.

What is claimed is:

1. In a process of producing a polyurethane by reacting a polyisocyanate, and at least one active hydrogen containing compound in the presence of a catalyst the improvement wherein the catalyst is a complex formed by mixing amidines containing the characteristic group

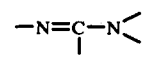

with 0.5 to 4 times the molar quantity of a metal compound corresponding to the formula $$Me X_n Y_m$$

in which
Me represents an $(n + m)$-valent metal,
X represents an aliphatic hydrocarbon radical with 1 to 18 carbon atoms, an aromatic hydrocarbon radical with 6 to 10 carbon atoms, or an araliphatic hydrocarbon radical with 7 to 15 carbon atoms,
Y represents an aliphatic $C_2$–$C_{18}$-carboxylate anion with a single negative charge and optionally containing olefinic double bonds and/or alcoholic hydroxyl groups, or a $C_5$–$C_{18}$-enolate anion carrying a single negative charge,
$n = 0$ to 2,
$m = 0$ to 4 with the proviso that $n + m$ together = 2 to 4.

2. The process of claim 1, wherein said complex is selected from the group consisting of 2,3-dimethyl-3,4,5,6-tetrahydropyrimidine and dibutyl tin dilaurate; 2,3-dimethyl-3,4,5,6-tetrahydropyrimidine and dibutyl tin-bis-ethyl hexoate; 2,3-dimethyl-3,4,5,6-tetrahydropyrimidine and diethyl tin diacetate; 2-methyl-3-cyclohexyl-3,4,5,6-tetrahydropyrimidine and dibutyl tin dilaurate; 2,3-dimethyl-3,4,5,6-tetrrahydropyrimidine and Mn(II)-acetylacetonate; 2.3-dimethyl-3,4,5,6-tetrahydropyrimidine and Ni(II)-acetylacetonate; N-methyl-imidazole and dibutyl tin dilaurate; N-methylimidazole and Mn(II)-acetylacetonate and N-methylimidazole and Fe(III)-acetylacetonate.

3. The process of claim 1, wherein said complex is based in quantities of from 0.001 to 4.00% by weight based on the total weight of active hydrogen containing material.

4. The process of claim 1, wherein said complex is based in quantities of from 0.01 to 0.8 percent by weight based on the total weight of active hydrogen containing material.

* * * * *